United States Patent [19]

Burruss

[11] 4,141,369

[45] Feb. 27, 1979

[54] NONCOMBUSTION SYSTEM FOR THE UTILIZATION OF TOBACCO AND OTHER SMOKING MATERIALS

[76] Inventor: Robert P. Burruss, 6433 79th St., Cabin John, Md. 20731

[21] Appl. No.: 761,794

[22] Filed: Jan. 24, 1977

[51] Int. Cl.$^2$ ............................................. A24F 1/00
[52] U.S. Cl. ............................... 131/171 A; 128/192
[58] Field of Search .................. 128/192; 131/170 A, 131/171 A, 8 A

[56] References Cited

U.S. PATENT DOCUMENTS

| | | | |
|---|---|---|---|
| 1,771,366 | 7/1930 | Wyss et al. | 128/192 |
| 1,949,778 | 3/1934 | Brown et al. | 128/192 |
| 2,104,266 | 1/1938 | McCormick | 131/170 A |
| 2,449,853 | 9/1948 | Karp | 128/192 |

Primary Examiner—Robert W. Michell
Assistant Examiner—V. Millin
Attorney, Agent, or Firm—John S. Roberts, Jr.

[57] ABSTRACT

An electrical device for the noncombustion utilization of tobacco and other smoking materials. The device consists of a canister or other appropriate container within which air is electrically heated to an appropriate temperature for volatilizing the desired components of smoking material previously inserted into a receptacle provided in the mouthpiece part of this invention. Volatilization takes place when the heated air is drawn through the smoking material contained in the mouthpiece assembly. The mixture of heated air and volatilized smoking material components is then drawn from the mouthpiece into the mouth and respiratory passages of the user of the device.

5 Claims, 6 Drawing Figures

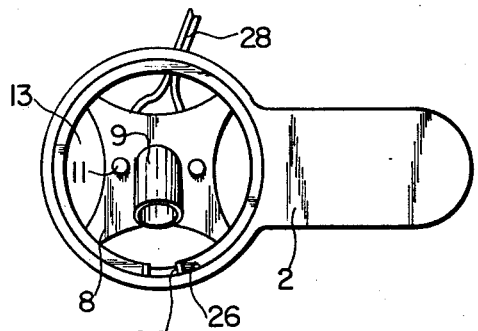
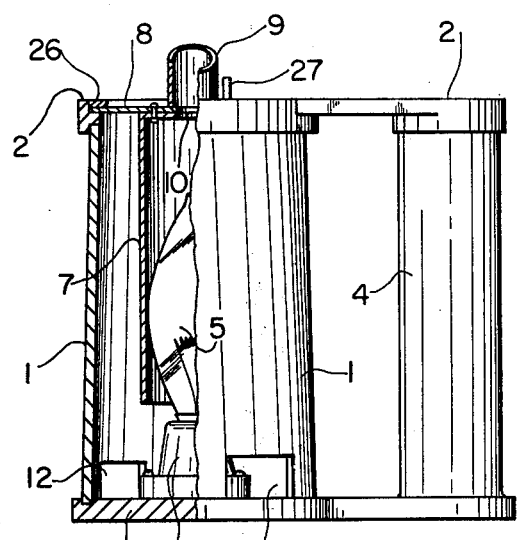
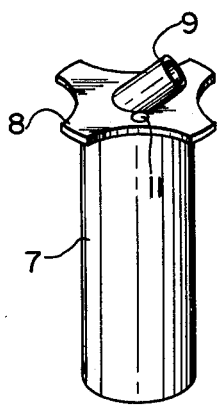
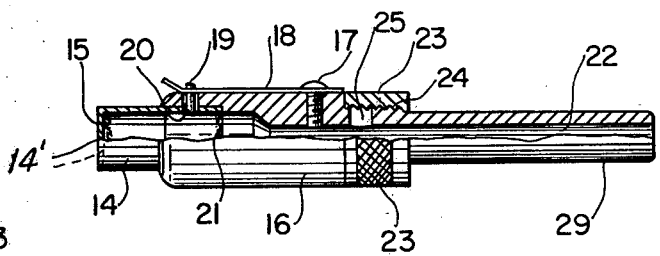
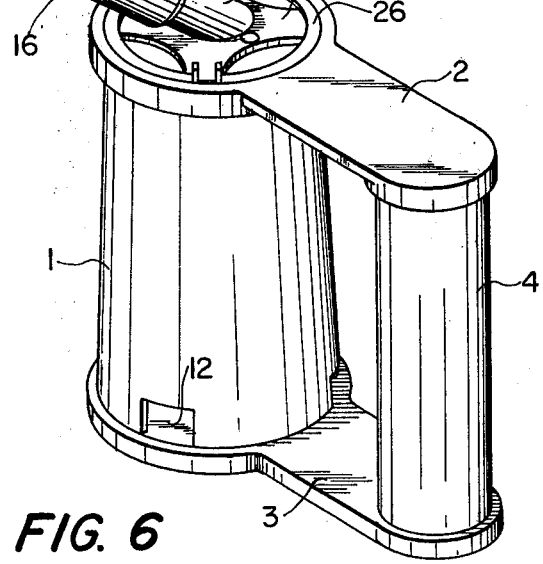
FIG. 1  FIG. 2  FIG. 3  FIG. 4  FIG. 5  FIG. 6

NONCOMBUSTION SYSTEM FOR THE UTILIZATION OF TOBACCO AND OTHER SMOKING MATERIALS

My invention relates to the improvement of means for utilizing tobacco and other smoking materials listed below through the noncombustion volatilization of the active ingredients to be inhaled. The volatilization is being effected by the application of heat to the smoking material by a combination of conduction and convection so that the temperature of the smoking material can be raised high enough to volatilize the active principals, but not sufficiently high to induce combustion or high-temperature thermal decomposition of organic materials not contributing to the purpose of tobacco use, or other smoking material use.

The term smoking material is intended to include any combustible organic material containing volatile ingredients which upon combustion are vaporized and can be drawn into the mouth and respiratory passages of a smoker. Such materials include tobacco, licorice, eucalyptus, teas, flower petals, and other herbs. Such smoking materials may be used alone or in various combinations with one another.

The traditional methods of tobacco smoking are based on the combustion of part of the tobacco, the resultant heat of combustion of which causes the vaporization of the volatile components of the unburned smoking material. The well-known disadvantage of such traditional methods of tobacco utilization is that the smoker not only inhales the desired taste and other volatile active ingredients, but also inhales the combustion by-products which are associated with cancer and diseases of the heart and lungs. Such products and by-products of combustion include carbon monoxide, benzo(a)pyrene, volatilized cadmium, nitrogen oxides, sulfur oxides, hydrogen sulfide, and a spectrum of heavy hydrocarbons which are either the direct result of combustion of organic material or are the result of the unnecessarily-high-temperature volatilization of ingredients in the unburned portion of the smoking material immediately adjacent to the combustion zone.

Previous inventions and methods related to the use of smoking materials have sought to eliminate the combustion products from the desirable gaseous ingredients. The earliest systems, and some presently in use, rely on the use of solid and aqueous filters of various kinds to remove portions of the disease-causing products of combustion.

Another method of eliminating combustion products from the spectrum of gaseous ingredients inhaled during the pleasurable utilization of smoking materials is through the administration of controlled amounts of heat from sources other than the combustion of the smoking material itself and in sufficient amount to vaporize the volatile ingredients of the smoking material without causing combustion or unnecessary thermal decomposition of the smoking material. Such methods have been based on each of the three modes of heat transfer — conduction, convection, radiation — and on combinations thereof. An example of a purely conductive system would be one where heat from a hot surface is conducted into the smoking material from which volatile materials are thence vaporized; the gases thus produced can be inhaled. An example of a purely convective system would be one in which air might be preheated to sufficient temperature than drawn through the smoking material so that the heat of the air is transferred to the smoking material, thereby raising the temperature of the smoking material sufficiently to drive the volatile fractions into the air flow, which carries the volatilized fractions to the mouth and respiratory organs of the smoker. An example of a purely radiative method would be one in which radiant energy is directed at the surface of smoking material thereby causing it to heat to a sufficient temperature to cause vaporization of the volatile fractions which can then be carried to the mouth and respiratory organs of the smoker via a flow of air passing adjacent to the radiantly-heated smoking material. Since such methods of smoking-material utilization do not entail combustion, no products of combustion, or products of high-temperature thermal decomposition are generated, thereby protecting the smoker from the bulk of the hazard of smoking. When tobacco is used in noncombustion systems of smoking, nicotine and its related chemical principals that are not generated by combustion, but which are intrinsic to the tobacco plant and essential to the taste and other desired effects of smoking, are some of the ingredients also vaporized in noncombustion tobacco-utilization systems. Nicotine is toxic, but chronic ingestion of small amounts has not been linked directly to disease.

The previously patented methods of noncombustion tobacco utilization rely on the administration to the smoking material of thermal energy generated by electrical resistance or by the combustion of material the combustion products of which are not inhaled directly by the smoker. In the method patented by Ellis et al. (3,258,015), "smoldering material" placed concentrically to the smoking material provides heat by conduction to the smoking material; the disadvantage is that in confined areas, both the smoker and adjacent nonsmokers are indirectly exposed to the products of combustion of the "smoldering material".

In my invention, the details of operation of which are listed below, the source of thermal energy is an electrically-heated element such as a lightbulb of appropriate power output or an electric-resistance heating element. The heating element heats to air in a chamber from which the heated air is thence drawn through the smoking material and into the mouth and respiratory passages of the user of my invention. When the hot air moves through the smoking material, part of its heat causes the vaporization of the volatile components of the smoking material, said volatile ingredients then, in a vapor state, enter the air flow and are likewise carried into the mouth and respiratory passages of the user. The temperature of the air flow, while sufficient to cause volatilization of the volatile components of the smoking material, is not sufficient to cause pyrolytic breakdown of the nonvolatile, cellulosic parts of the smoking material, thereby not causing the generation of the complex hydrocarbon substances associated with the usual methods of tobacco and smoking-material utilization.

The drawings show in schematic representation the structure of my invention and some of its components:

FIG. 1 shows a top view of the base assembly part of my invention.

FIG. 2 shows a side view, partially cutaway, of the base assembly.

FIG. 3 shows a perspective view of the hot-air storage chamber which is also shown in place in FIGS. 1 and 2.

FIG. 4 shows a partially cutaway side view of the mouthpiece part of my invention.

FIG. 5 shows a perspective view of the snap ring which is shown in place in FIGS. 1 and 2.

FIG. 6 shows a perspective view of the base and mouthpiece assemblies together.

Referring to FIGS. 1 and 2, which show respectively the top and side views of the air-heater part of my invention (FIG. 2 being a cutaway view showing the internal parts), the principal components of construction and their relationship to one another become evident. Cylinder 1 is an outer container or envelope which as with top 2 and base 3 and handle 4 is made of cast phenolic plastic or other material of suitable low thermal conductivity and high temperature capability. Lightbulb 5 situated in socket 6 provides the heat for the operation of my invention, though any suitable electrically-heated resistance element would also serve this purpose. Air heated by the lightbulb/heating element is stored in the hot-air chamber 7 which with flange 8, tube 9 and connecting hole 10 constitutes the hot-air chamber assembly shown in FIG. 3, where rivets 11, or other fastening devices hold the assembly together.

The use of a lightbulb as a heating element has the advantage of readily indicating to the user that the device is turned on — that is, it serves the purpose of an indicator light in addition to being a heating element. The light can be seen through the multiplicity of vent holes provided in the construction of the device. A secondary advantage of the lightbulb as a heating element is that replacement bulbs can be readily purchased by the user at any retail outlet of lighting equipment.

In FIG. 2, vent holes 12 in the base of envelope 1 allow air to move by natural convection into the device where it is either heated and stored in chamber 7 or convects upwards through the annular space between the outer surface of chamber 7 and the inner surface of envelope 1 and thence out of the device through the passages 13 (FIG. 1) in the top of the device. This convective air movement allows removal of excess heat from the inner surface of envelope 1 thus minimizing the external surface temperature of envelope 1.

FIG. 4 is a partial cutaway view of the mouthpiece 16 and smoking-material-holder part 14 of my invention. Cylindrical container 14 with small-mesh screen 15 holds the smoking material. The outer diameter of container 14 is such as to allow container 14 to be inserted snuggly into the body 16 of the mouthpiece and to latch into place by way of the spring-latch mechanism consisting of screw 17, flat spring 18 and pin 19 which enters hole 20 in container 14. (Any similar latching device will suffice, and other methods might be used to hold the smoking-material container 14 in place in mouthpiece 16, such as by means of machined threads on the container 14 and in the mouthpiece 16.) Screen 21 prevents the movement of smoking material up the passage 22 and into the mouth of the user during use. The entire mouthpiece assembly is affixed to the base assembly during use in the manner shown in FIG. 6, wherein it is evident that container 14 fits within and concentric to tube 9.

A fixture which may or may not be included in the construction of the mouthpiece assembly is the air valve which allows cool air to be mixed with the hot-air flow in passage 22, thus cooling the temperature of the flow to a level agreeable to the user. Said valve may consist of any system allowing control over the amount of cooling air entering the hot flow, and in this schematic example consists of a knurled metal ring 23 having internal threads 24, corresponding to male threads on the mouthpiece body 16, such that turning of the knurled metal ring 23 allows hole 25 to be uncovered to the desired extent to introduce cool air into the air flow in passage 22.

FIG. 5 shows a snap ring 26 with tangs 27, said ring being situated as shown in FIGS. 1 and 2 where it holds the hot-air chamber assembly (shown in FIG. 3) in place and allows easy removal of the heat chamber so that lightbulb 5 of other heating element may be serviced, adjusted or replaced. Ring 26 also allows the hot-air chamber assembly to be rotated in top 2 to an optimum position relative to handle 4 for comfortable use by both right-handed and left-handed users.

In FIG. 1, electrical cord 28 connects at one end to the socket 6 and at the other to a suitable supply of electrical power. An electrical switching device, not shown, may be incorporated into the structure of my invention, or may be included on electrical cord 28.

In the following description of the operation of my invention, the attainment of my objective will be made clear:

Container 14 shown in FIG. 4 is removed from the body 16 of the mouthpiece and is filled with smoking material of a sufficiently finely divided nature that it falls easily into container 14. The container 14 is then inserted back into the mouthpiece body 16 and latched securely by the latch mechanism consisting of parts 17, 18, 19 and hole 20 in the smoking-material container.

Electrical connection is made between the lightbulb/heating element 5 and a suitable source of electricity, by means of electrical cord 28 shown in FIG. 1. When the bulb is turned on, heat energy radiated from it heats the air in hot-air chamber 7 to a suitably high temperature. The smoking-material container 14 of the mouthpiece assembly is inserted into tube 9 which connects by way of hole 10 to the hot-air chamber 7. The user provides suction on stem 29 so that heated air flows from the hot-air chamber 7 into the smoking-material container 14 through one or more apertures 14' where the heated air causes the volatilization of the desired ingredients of the smoking material. The volatilized ingredients are thence carried in the air flow through passage 22 in stem 29 and thence into the mouth and respiratory passages of the user. The air valve assembly, consisting of the knurled, internally-threaded metal ring 23 and hole 25 in the body 16 of the mouthpiece assembly, can be adjusted by turning the ring to allow cool air to flow from the outside of the mouthpiece into the hot-air flow in passage 22, thereby cooling the flow to a level agreeable to the user.

When the smoking material is depleted of its desired volatile ingredients, the electrical connection is broken, the mouthpiece assembly is removed from tube 9, the smoking-material container 14 is unlatched from the mouthpiece, and the spent material is poured out. The process can then be repeated in the manner stated above.

In the event that the lightbulb heating element needs to be adjusted or replaced, tangs 27 on snap ring 26 can be squeezed together between the thumb and forefinger, thus enabling the removal of the snap ring and the hot-air chamber assembly (FIG. 3) from the base assembly (FIGS. 1 and 2) thereby making the lightbulb/heating element 5 accessible through the top 2 of the base assembly.

The advantages of my invention over the "medicating apparatus" patented by Wyss et al. (No. 1,771,366), which operates on a similar principle of electrically preheating air which is thence drawn through a "tampon" soaked in a volatile medicament, is: (1) my invention incorporates a storage chamber for the hot air, and (2) by the nature of its construction, my invention allows the use of much higher operating temperatures needed for the volatilization of the desirable volatile components in common smoking materials. My experiments indicate conclusively that in order for the Wyss device to volatilize the desired components of tobacco and other smoking materials, it would have to operate at a temperature so high that it would have to be constructed entirely out of metal or refractory ceramic material and that the temperature of its external surfaces would exceed 300° F. during operation — much too hot to be easily handled or to be inserted into the mouth or nasal openings, as intended.

The design of my invention is such as to enable the generation of hot air in sufficient volume and of sufficient temperature to volatilize without combustion the desired components of tobacco and other smoking materials, while at the same time having sufficiently low external surface temperature so as not to cause injury if touched by the skin of the user or adjacent persons.

I claim as my invention:

1. In an arrangement for utilizing tobacco and the like smoking materials without effecting combustion thereof, a side and bottom wall means defining a casing, said side wall means having openings therein adjacent the bottom wall means, a tubular chamber suspended within said casing and supported by said casing, said chamber being open at its lower end, heating means within said chamber for imparting heat to air entering the same through said openings and said open lower end, a tubular conduit in communication with the upper end of said chamber, a tubular mouthpiece means, an apertured tubular smoking material container removably arranged within one end of said mouthpiece means and having a length such as to protrude therefrom, said container being dimensioned such as to telescopically fit within said tubular conduit whereby to communicate air heated in the aforementioned chamber through said container to the mouth and respiratory passages of the user by way of the mouthpiece-contained smoking material; the heat energy in the heated air being imparted by convective and conductive transfer mechanisms to the smoking material wherefrom the volatile ingredients are evaporated away from the nonvolatile cellulosic components of the smoking material and are thence carried as a vapor in the heated air stream to the mouth and respiratory passages of the user.

2. The arrangement as claimed in claim 1 wherein said heating means comprises an incandescent light bulb supported within said suspended chamber.

3. The arrangement as claimed in claim 1 and further including air valve means operably associated with said mouthpiece means up stream of said smoking material container and operable to admit cool air to admix with the heated air flowing through said mouthpiece means.

4. The arrangement as claimed in claim 1 and further including handle means extending from said casing permitting the user to handle and move said arrangement without contacting said casing.

5. The arrangement as claimed in claim 1 and further including latch means to hold said container within said mouthpiece means.

* * * * *